US010717994B2

(12) United States Patent
Chuang et al.

(10) Patent No.: US 10,717,994 B2
(45) Date of Patent: Jul. 21, 2020

(54) RECOMBINANT POLYPEPTIDE FOR ENHANCING CELL TRANSDUCTION EFFICIENCY OF A TARGET AGENT

(71) Applicant: Agricultural Technology Research Institute, Hsinchu (TW)

(72) Inventors: Chin-Kai Chuang, Hsinchu (TW); Yu-Hsiu Su, Hsinchu (TW); Tzuyin Lin, Hsinchu (TW)

(73) Assignee: AGRICULTURAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 15/380,253

(22) Filed: Dec. 15, 2016

(65) Prior Publication Data

US 2018/0170981 A1 Jun. 21, 2018

(51) Int. Cl.

| | |
|---|---|
| ***A61K 38/04*** | (2006.01) |
| ***A61K 47/64*** | (2017.01) |
| ***C12N 15/09*** | (2006.01) |
| ***C12N 15/87*** | (2006.01) |
| ***C07K 14/245*** | (2006.01) |

(52) U.S. Cl.

CPC .............. *C12N 15/87* (2013.01); *A61K 47/64* (2017.08); *C07K 14/245* (2013.01); *C07K 2319/10* (2013.01)

(58) Field of Classification Search

CPC ...... A61K 38/04; A61K 38/162; A61K 47/64; A61K 47/645; C07K 2319/10; C12N 15/09; C12N 15/87

See application file for complete search history.

(56) References Cited

U.S. PATENT DOCUMENTS

| | | | | |
|---|---|---|---|---|
| 7,049,286 | B2 * | 5/2006 | Tchelingerian .......... | C07K 7/06 424/133.1 |
| 7,759,461 | B2 * | 7/2010 | Chen .................... | C07K 14/005 530/350 |
| 8,410,045 | B2 | 4/2013 | Michel et al. | |
| 2013/0137644 | A1 | 5/2013 | Alluis et al. | |
| 2015/0004192 | A1 * | 1/2015 | Chuang .................. | C07K 14/47 424/193.1 |
| 2015/0299756 | A1 * | 10/2015 | Hishiya .................. | C12N 9/644 514/44 R |

FOREIGN PATENT DOCUMENTS

WO WO 07/113687 * 10/2007

OTHER PUBLICATIONS

De Coupade et al, Biochem J. 390: 407-418, 2005.*
Yang et al, J. Biol. Chem. 285(33): 25666-25676, 2010.*

* cited by examiner

*Primary Examiner* — Kevin K Hill
(74) *Attorney, Agent, or Firm* — WPAT, PC

(57) ABSTRACT

The invention provides a recombinant polypeptide X—Y for enhancing cell transduction efficiency of a target agent, wherein X is a cell penetrating peptide DPV3, and Y is an Hsp40-J domain. Also provided is a method for enhancing cell transduction efficiency of a target agent, comprising conjugating/attaching said target agent with a recombinant polypeptide X—Y, wherein X is a cell penetrating peptide DPV3, and Y is an Hsp40-J domain. Further provided is a pharmaceutical composition comprising a therapeutic agent, wherein said therapeutic agent is modified by conjugating/attaching with a recombinant polypeptide X—Y, wherein X is a cell penetrating peptide DPV3, and Y is an Hsp40-J domain.

6 Claims, 5 Drawing Sheets

Specification includes a Sequence Listing.

RECOMBINANT POLYPEPTIDE FOR ENHANCING CELL TRANSDUCTION EFFICIENCY OF A TARGET AGENT

CROSS-REFERENCE TO RELATED APPLICATION

This application is a divisional application of U.S. patent application Ser. No. 14/319,691, filed Jun. 30, 2014, which claims the priority to Taiwan Patent Application No. 102123326, filed Jun. 28, 2013, and Taiwan Patent Application No. 102131721, filed Sep. 3, 2013. The contents of the prior applications are incorporated herein by its entirety.

FIELD OF THE INVENTION

The present invention pertains to a recombinant polypeptide for enhancing cell transduction efficiency of a target agent. The invention also pertains to a method for enhancing cell transduction efficiency of a target agent. The target agent may be a therapeutic agent. The target agent includes but is not limited to a chemical agent, a protein, a nucleic acid, or a vaccine.

BACKGROUND OF THE INVENTION

A recombinant protein expression system that improves yield and immunogenicity has been disclosed in U.S. Ser. No. 12/149,606, filed 5 May 2008, now U.S. Pat. No. 7,524,648 and U.S. Ser. No. 12/406,789, now U.S. Pat. No. 7,759,461; the contents of which are incorporated herein by reference. Said expression system includes the protein transduction domain (PTD) and Hsp40-J domain, and may improve yield and immunogenicity of the recombinant protein to be expressed.

U.S. Pat. No. 8,410,045 discloses that conjugating camptothecin with a cell penetrating peptide (CPP) may increase solubility, modify the pharmacokinetics, metabolism and tissue distribution properties of camptothecin.

US 20130137644 A1 discloses that conjugating a nucleic acid with a CPP may improve delivery efficacy of said nucleic acid into cells.

There is still a need to develop a system or method that further enhances the cell transduction efficiency of an active agent.

BRIEF SUMMARY OF THE INVENTION

In accordance with the invention, there is provided a recombinant polypeptide for enhancing cell transduction efficiency of a target agent, having the following formula (I): X—Y (I); wherein X represents a cell penetrating peptide DPV3, and Y represents an Hsp40-J domain. For example, a modified target agent may have the following formula (II): X—Y-target agent (II); wherein X represents a cell penetrating peptide DPV3, and Y represents an Hsp40-J domain.

According to the present invention, attaching DPV3 and Hsp40-J domain to a protein can significant enhance its cell transduction efficiency, and typically results in efficiency better than that using liposome delivery.

In another aspect, the present invention provides a method for enhancing cell transduction efficiency of a target agent, comprising conjugating/attaching said target agent with a recombinant polypeptide having the following formula (I): X—Y (I); wherein X represents a cell penetrating peptide DPV3, and Y represents an Hsp40-J domain.

According to the present invention, the target agent may be a therapeutic agent. Preferably, the target agent includes but is not limited to a chemical agent, a protein, a nucleic acid, or a vaccine.

Also provided is a pharmaceutical composition comprising a therapeutic agent, wherein said therapeutic agent is modified by conjugating/attaching with a recombinant polypeptide having the following formula (I): X—Y (I); wherein X represents a cell penetrating peptide DPV3, and Y represents an Hsp40-J domain.

In further aspect, the present invention provides an expression construct for producing a recombinant protein with enhanced cell transduction efficiency by a host cell, comprising a nucleic acid segment consisting essentially of a nucleotide sequence coding for DPV3, a nucleotide sequence coding for Hsp40-J domain, and a nucleotide sequence coding for the recombinant protein, the nucleic acid segment being operatively linked to host specific transcription and translation regulatory elements for the host cell.

The various embodiments of the present invention are described in details below. Other p-characteristics of the present invention will be clearly presented by the following detailed descriptions and drawings about the various embodiments and claims.

BRIEF DESCRIPTION OF THE SEVERAL VIEWS OF THE DRAWINGS

For the purpose of illustrating the invention, there are shown in the drawings embodiments which are presently preferred. It should be understood, however, that the invention is not limited to the preferred embodiments shown.

In the drawings:

In FIG. 4A, two recombinant protein expression constructs, DPV3-J-DsRed and DPV3-DsRed, in different concentrations (5, 10, 20 and 40 μg/mL) were respectively incubated with Huh7 cells for 2 hours, and the fluorescence intensity of DsRed in cells was detected subsequently. In FIG. 4B, two recombinant protein expression constructs, DPV3-J-DsRed and DPV3-DsRed (both 40 μg/mL) were respectively incubated with Huh7 cells for 0.5, 1, 2, 4 and 6 hours, and the fluorescence intensity of DsRed in cells was detected subsequently. In FIG. 4C, recombinant proteins, DPV3-J-DsRed and DPV3-DsRed, in different concentrations (0.05, 0.5, 2 and 5 μg/mL) were respectively incubated with Huh7 cells for 2 hours, and the fluorescence intensity of DsRed in cell lysates was detected subsequently.

DETAILED DESCRIPTION OF THE INVENTION

Figure 1A:
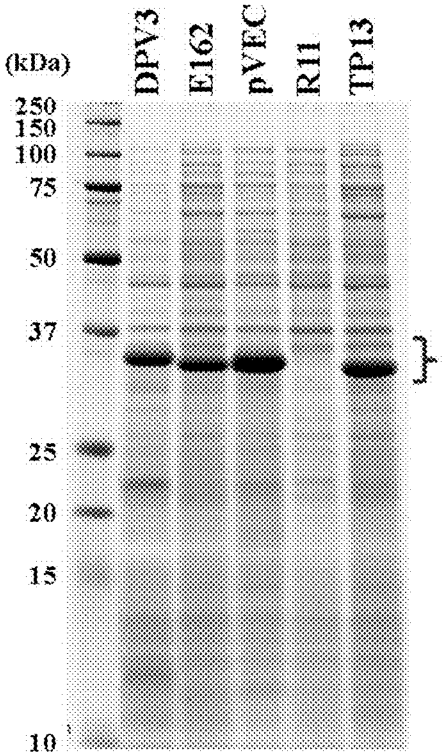
FIG. 1A shows SDS-PAGE results of *E coli.* whole cell lysates containing expressed recombinant proteins: DPV3-DsRed (DPV3), E162-DsRed (E162), pVEC-DsRed (pVEC), R11-DsRed (R11), and TP13-DsRed (TP13).

By the term “recombinant protein” as it is used herein is meant a recombinant molecule and usually a protein or peptide sequence covalently linked (i.e. fused) to a protein or peptide sequence by recombinant, chemical or other suitable method. If desired, the recombinant molecule can be fused at one or several sites through a peptide linker sequence. That peptide sequence can include one or more sites for cleavage by a host cell induced protease.

A “polypeptide” refers to any polymer preferably consisting essentially of any of the 20 natural amino acids regardless of its size. Although the term “protein” is often used in reference to relatively large proteins, and “peptide” is often used in reference to small polypeptides, use of these terms in the field often overlaps.

In one aspect, the present invention provides a recombinant polypeptide for enhancing cell transduction efficiency of a target agent, having the following formula (I):

$$X—Y \quad (I);$$

wherein X represents a cell penetrating peptide DPV3, and Y represents an Hsp40-J domain.

For example, a modified target agent may have the following formula (II):

$$X—Y\text{-target agent} \quad (II);$$

wherein X represents a cell penetrating peptide DPV3, and Y represents an Hsp40-J domain.

In another aspect, the present invention provides a method for enhancing cell transduction efficiency of a target agent, comprising conjugating/attaching said target agent with a recombinant polypeptide having the following formula (I):

$$X—Y \quad (I);$$

wherein X represents a cell penetrating peptide DPV3, and Y represents an Hsp40-J domain.

The target agent may be a therapeutic agent. Preferably, the target agent includes but is not limited to a chemical agent, a protein, a nucleic acid, or a vaccine.

The recombinant polypeptide X—Y may be conjugated/attached to a target agent by any method known in the art. For example, methods disclosed in U.S. Pat. Nos. 8,410,045, 8,518,871, and US 20130137644 A1, the entirety of which is incorporated herein by reference.

According to certain embodiments of the present invention, the DPV3 has a sequence comprising SEQ ID NO: 1. In one embodiment, the DPV3 consists of SEQ ID NO: 1. SEQ ID NO: 2 is an example of a nucleotide sequence coding for a peptide of SEQ ID NO: 1. In another embodiment of the present invention, the DPV3 has a sequence comprising SEQ ID NO: 5. SEQ ID NO: 6 is an example of a nucleotide sequence coding for a peptide of SEQ ID NO: 5. Sequences equivalent to SEQ ID NO: 1 or NO: 5 may also be used in the invention.

The Hsp40-J domain may be selected from a group consisting of Hsp40-J domains of subtypes A, B and C. For example, 41 human genome DnaJ/Hsp40 proteins containing J domains or J-like domains (Qiu et al., Cell. Mol. Life Sci. 63: 2560-2570 (2006)). According to one embodiment of the present invention, the HSP40-J domain has a sequence comprising SEQ ID NO: 3. In one further embodiment, the HSP40-J domain consists of SEQ ID NO: 3. SEQ ID NO: 4 is an example of a nucleotide sequence coding for a peptide of SEQ ID NO: 3.

In still another aspect, the present invention provides a pharmaceutical composition comprising a therapeutic agent, wherein said therapeutic agent is modified by conjugating/attaching with a recombinant polypeptide having the following formula (I):

$$X—Y \quad (I);$$

wherein X represents a cell penetrating peptide DPV3, and Y represents an Hsp40-J domain.

In further aspect, the present invention provides an expression construct for producing a recombinant protein with enhanced cell transduction efficiency by a host cell, comprising a nucleic acid segment consisting essentially of a nucleotide sequence coding for DPV3, a nucleotide sequence coding for Hsp40-J domain, and a nucleotide sequence coding for the recombinant protein, the nucleic acid segment being operatively linked to host specific transcription and translation regulatory elements for the host cell. Such an expression system was found in the present invention to have at least the following advantages: the recombinant protein produced therefrom exhibits enhanced cell transduction efficiency, and the produced recombinant protein is secreted into culture media and can be derived by isolation without disrupting cells or other complicated steps.

In another aspect, the present invention provides a method for producing a recombinant protein with enhanced cell transduction efficiency, comprising transforming the expression construct into a host cell, and collecting and isolating the recombinant protein from the host cell.

Further, the present invention also provides a method of delivering a therapeutic agent into a subject cell, comprising attaching DPV3- Hsp40-J domain to the therapeutic agent to obtain a modified therapeutic agent, and contacting the subject cell with modified therapeutic agent.

In one further aspect, the invention provides a pharmaceutical composition comprising a therapeutic agent, wherein the therapeutic agent is modified by attaching with DPV3-Hsp40-J domain.

According to certain embodiments of the present invention, the DPV3 has a peptide sequence comprising SEQ ID NO: 1. In one embodiment, the DPV3 has a peptide sequence consisting of SEQ ID NO: 1. SEQ ID NO: 2 is an example of a nucleotide sequence coding for a peptide of SEQ ID NO: 1. In another embodiment of the present invention, the DPV3 has a peptide sequence comprising SEQ ID NO: 5. SEQ ID NO: 6 is an example of a nucleotide sequence coding for a peptide of SEQ ID NO: 5. Sequences equivalent to SEQ ID NO: 1 or NO: 5 may also be used in the invention.

The Hsp40-J domain may be selected from a group consisting of Hsp40-J domains of subtypes A, B and C. For example, 41 human genome DnaJ/Hsp40 proteins containing J domains or J-like domains (Qiu et al., Cell. Mol. Life Sci. 63: 2560-2570 (2006)). According to one embodiment of the present invention, the HSP40-J domain has a peptide sequence comprising SEQ ID NO: 3. In one further embodiment, the HSP40-J domain has a peptide sequence consisting of SEQ ID NO: 3. SEQ ID NO: 4 is an example of a nucleotide sequence coding for a peptide of SEQ ID NO: 3.

The nucleotide sequences of the invention, particularly DNA sequences coding for the recombinant proteins of the invention, include but are not limited to, those carried by a vector suited for extrachromosomal replication such as a phage, virus, plasmid phagemid, cosmid, YAC or episome. In particular, a DNA vector that coding for a desired recombinant protein can be used to facilitate preparative methods described herein and to obtain significant quantities of the recombinant protein. The DNA sequence can be inserted into an appropriate vector, i.e., a vector that contains the necessary elements for the transcription and translation of the inserted protein-coding sequence. A variety of host-vector systems may be utilized in the invention. One example is a eukaryotic cell, such as *E. coli*. The host-vector systems also include mammalian cell systems infected with virus, insect cell systems infected with virus; microorganisms such as yeast containing yeast vectors, or bacteria transformed with bacteriophage DNA, plasmid DNA or cosmid DNA. Depending on the host-vector system utilized, and one of a number of suitable transcription and translation elements may be used. For example, the vector may contain promoters such as bacterial T7 promoter and inducible operator such as lac operator to regulate the transcription.

Other vectors and constructs include chromosomal, non chromosomal and synthetic DNA sequences; bacterial plasmids; phage DNA; baculovirus; yeast plasmids; yeast artificial chromosomes (YACs); vectors derived from combination of plasmids and phage DNA; shuttle vectors derived from combinations of plasmids and viral DNA; viral DNA, such as vaccinia, adenovirus, avian influenza virus, and pseudorabies. However, any other vector may be used for preparation of a nucleic acid expression construct as long as it is replicable and viable in the host cell of interest. The nucleic acid sequence may be flanked by a number of restriction endonuclease sites for isolation and cloning into any desired vector. There are also protein identification or purification tags such as EE, $(His)_6$, HA or MYC added to facilitate subsequent purification of the recombinant protein. In addition, the nucleic acid expression construct may also contain a transcription terminator. For example, the vector may contain T7 terminator for terminating the transcription of the nucleic acid sequence.

In accordance with one specific example of the invention, a recombinant protein may be expressed by using a nucleotide sequence which comprises a nucleotide sequence coding for DPV3, for example, SEQ ID No: 2, a nucleotide sequence coding for Hsp40-J domain, for example, SEQ ID No: 4, and a nucleotide sequence coding for the recombinant protein, for example, a red fluorescence protein, wherein the nucleotide sequence operatively is linked to host specific transcription and translation regulatory elements.

In another embodiment, a recombinant protein may be expressed by using a nucleotide sequence which comprises a nucleotide sequence coding for DPV3, for example, SEQ ID No: 6, a nucleotide sequence coding for Hsp40-J domain, for example, SEQ ID No: 4 and a nucleotide sequence coding for a recombinant protein, for example, a red fluorescence protein, wherein the nucleotide sequence operatively is linked to host specific transcription and translation regulatory elements.

Recombinant proteins conjugated/attached with DPV3-Hsp40-J domain may be efficiently transduced into target cells or groups of such cells. Transduction efficiency may be monitored and quantified. For example, one approach involves an in vitro assay that measures uptake of the recombinant protein by the cell. The assay includes detectably-labeling the recombinant protein with e.g., a radioactive atom, fluorescent, phosphorescent, or luminescent tag (e.g. fluorescein, rhodamine, FITC) and then measuring uptake of the labeled recombinant protein. Alternatively, the recombinant protein can be labeled with an enzyme capable of forming a detectable label such as horseradish peroxidase, β-galactosidase, chloramphenicol acetyl transferase or luciferase. Uptake can be measure by several conventional methods such as by quantifying labeled cells in a standard cell sorter (e.g., FACS), by fluorescence microscopy or by autoradiography.

As mentioned generally above, a host cell may be used for preparative purposes to propagate nucleic acid encoding a desired recombinant protein, Thus, the host cell may be a higher eukaryotic cell, such as mammalian cell, or a lower eukaryotic cell, such as a yeast cell, or the host cell can be a prokaryotic cell, such as a bacterial cell. Representative examples of appropriate host cells according to the present invention include, but need not be limited to, bacterial cells, such as *E coli., Streptomyces, Salmonella typhimurium;* fungal cells, such as yeast; insect cells, such as *Drosophila* S2 and *Spodoptera* Sf9, animal cells, such as MDCK, Hep-2, CHO or COS; human cells, such as Jurkat or 293 cells; adenovirus; plant cells, or any other cells already adapted to in vitro propagation or so established de novo. The selection of an appropriate host cell is deemed to be within the scope of those skilled in the art from the teachings herein.

In addition, nucleic acid encoding a desired recombinant protein can be introduced into the host cells by standard techniques for transfecting cells. The term “transfecting” or “transfection” is intended to encompass all conventional technique for introducing nucleic acid into host cells, including calcium phosphate co-precipitation, DEAE dextran-mediated transfection, lipofection, electroporation, microinjection, viral transduction and/or integration.

The recombinant proteins of the present invention may be separated and purified by appropriate combination of known techniques. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electrical charge such as ion-exchange column chromatography, methods utilizing specific affinity such as affinity chromatography, method utilizing a difference in hydrophobicity such as reverse-phase high performance liquid chromatography and method utilizing a difference in isoelectric point, such as isoelectric focusing electrophoresis, metal affinity columns, such as Ni-NTA.

The invention will now be described in further detail with reference to the following specific, non-limiting examples.

EXAMPLE 1

Preparation of pET22b-PTD1 -J-DsRed Expression Construct

The pET22b plasmid (Novagen, Madison, Wis.) was utilized to construct pET22b-PTD1-J vector which includes a nucleotide sequence coding for a PTD transduction domain, a nucleotide sequence coding for Hsp40-J domain, and a nucleotide sequence coding for DsRed. The 5' end of the oliginucleotides coding for PTD1 for *E coli.* was phosphorylated by polynucleotide kinase before annealing to double strand form in order to be inserted into the pET22b plasmid which was co-digested by NdeI and BamHI and dephosphorylated by calf intestine alkaline phosphatase (CIAP) to create pET22b-PTD1.

The oliginucleotides of HSP40-J domain synthesized by PCR was cloned into pGEM-T Easy vector (Promega) for single colony selection and DNA sequencing. Plasmid with HSP40-J domain was co-digested by BamHI and EcoRI to remove the 0.2 kb inserted DNA fragment from pGEM-T Easy vector. This DNA fragment was then inserted into pET22b-PTD1 vector which was treated by BamHI/EcoRI and CIAP to create pET22b-PTD1-J1 expression vector.

Assembly PCR

Oligonucleotide sets were utilized to synthesize codon optimized cDNA. 0.5 μM of F1 and R1 as well as 0.05 μM of F2, F3, R3, R2 and so on were adjusted in PCR reaction mixture. The reaction conditions were 94° C. for 2 minutes followed by 20 cycles of 94° C. for 20 sec/40° C. for 40 sec/72° C. for 20 seconds and extension at 72° C. for 5 minutes. The PCR products were cloned into pGEM-T Easy for plasmid DNA isolation and DNA sequencing.

Amplifying pDsRed monomer N1 (Clontech) plasmid coding for a nucleotide sequence of DsRed protein. The PCR products were cloned into pGEM-T Easy vector (Promega) for single colony selection and DNA sequencing. The DNA coding for DsRed protein are flanked by EcoRI and XhoI sites in order to be inserted into pET22b-PTD1-J1 vector and constructed to be pET22b-PTD1-J1-DsRed expression vector (hereinafter referred to as pET22b-PTD-J-DsRed).

EXAMPLE 2

Construction of pET22b-CPP-DsRed and pET22b-CPP-J-DsRed Expression Vector

Five cell-penetrating peptide (CPP) proteins, DPV3 (SEQ NO: 1 or 5), E162, pVEC, R11 and TP13, were selected for construction of the expression vectors. Oligonucleotides of paired primers were treated in a solution (10 mMTris-HCl, pH 8.0/1 mM EDTA, pH 8.0/0.3 M NaCl) for 30 minutes at 60° C. The solution was then cooled slowly to room temperature for 60 minutes to form double strands. Subsequently, pET22b plasmid co-digested by NdeI and EcoRI was inserted to form pET22b-DPV3, pET22b-E162, pET22b-pVEC3, pET22b-R11 and pET22b-TP13, respectively.

pET22b-DPV3, pET22b-E162, pET22b-pVEC3, pET22b-R11 and pET22b-TP13 were digested by EcoRI and XhoI, and the aforementioned DNA segment of DsRed was inserted to form pET22b-DPV3-DsRed, pET22b-E162-DsRed, pET22b-pVEC3-DsRed, pET22b-R11-DsRed and pET22b-TP13-DsRed, respectively.

pET22b-DPV3, pET22b-E162, pET22b-pVEC3, pET22b-R11 and pET22b-TP13 was digested by BamHI and XhoI, and DNA segment of J-DsRed derived by digesting pET22b-PTD-J-DsRed with the same enzyme to form pET22b-DPV3-J-DsRed, pET22b-E162-J-DsRed, pET22b-pVEC3-J-DsRed, pET22b-R11-J-DsRed and pET22b-TP13-J-DsRed, respectively.

EXAMPLE 3

Expression of Recombinant Proteins

The pET22b-CPP-DsRed and pET22b-CPP-J-DsRed expression vectors prepared in Example 2 were transformed into *E. coli* Rosetta (Novagen) competent cells. The cells were cultured at 37° C. with 2×YT media (0.4% glucose, 30 μg/mL chloromycetin and 50 μg/mL ampicillin), amplified to OD600=0.6, and then induced by 1 mM IPTG and continually cultured for 4 hours.

In order to analyze the recombinant proteins released to the media, the *E coli.* culture was centrifuged at 20,000 g for 30 minutes, and the supernatant was collected and concentrated by 10 times using Centricon (Y3, Millipore). 30 μL protein sample was taken and separated by 12% SDS-PAGE. To analyze the recombinant proteins in the cells, the cells were centrifuged at 10,000 g for 10 minutes and sonicated, 600 units soluble and insoluble proteins corresponding to 0.1 OD were taken and separated by 12% SDS-PAGE and stained with Coomassie Brilliant Blue R250. Soluble CPP-DsRed and CPP-J-DsRed recombinant proteins were further purified by Ni-Sepharose 6 Fast Flow affinity column (17-5318-02, GE) according to the manufacturer's guideline.

Figure 1B:
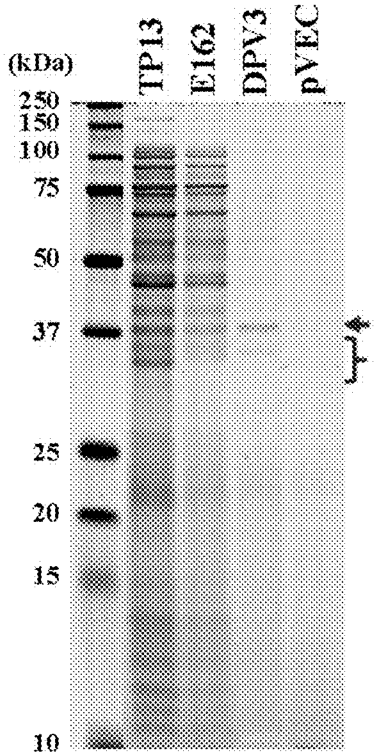
FIG. 1B shows SDS-PAGE results of the culture media of the following groups: TP13-DsRed (TP13), E162-DsRed (E162), DPV3-DsRed (DPV3), and pVEC-DsRed (pVEC). Endogenic 38 kDa protein from the host cell was used as a standard molecular weight marker (indicated with an arrow). Positions of recombinant DsRed proteins are indicated with a bracket.
Figure 1C:
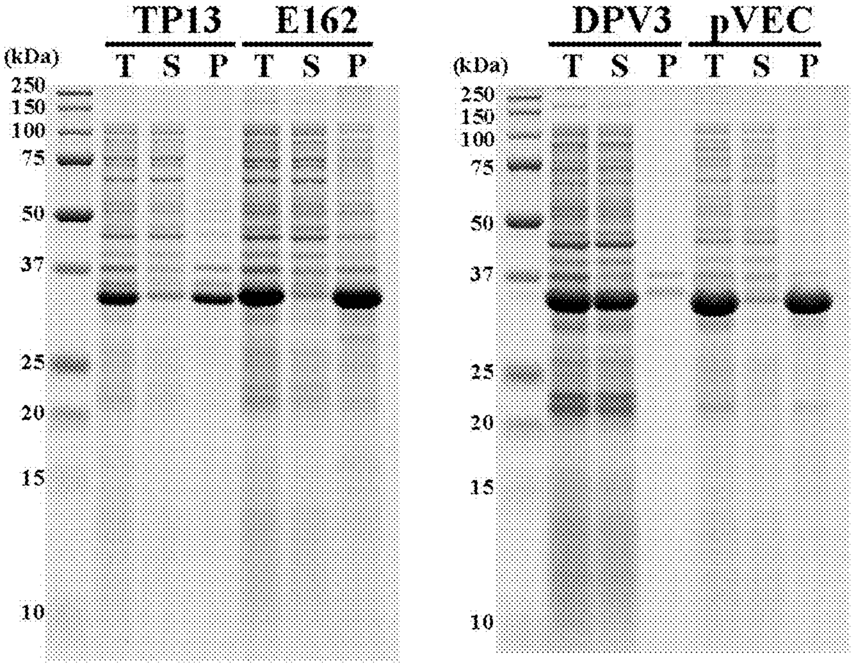
FIG. 1C shows SDS-PAGE results of *E coli.* whole cell lysates (T) containing expressed recombinant proteins: TP13-DsRed (TP13), E162-DsRed (E162), DPV3-DsRed (DPV3), and pVEC-DsRed (pVEC), centrifuged and separated into soluble (S) and insoluble (P) parts.

The expression of CPP-DsRed recombinant protein in *E Coli.* was shown in FIG. 1, wherein the expression of R11-DsRed recombinant protein can hardly be detected from cell lysates of *E Coli.* (see FIG. 1A), and therefore only the other five recombinant proteins were subsequently analyzed. After homogenizing by sonication, cell lysates were separated into soluble part (S) and insoluble part (P) by centrifugation. A lot of DPV3-DsRed recombinant proteins were found in the soluble part. On the other hand, TP13-DsRed, E162-DsRed and pVEC-DsRed recombinant proteins mainly exist in the insoluble part (see FIG. 1C).

In addition, to analyze the proteins induced by IPTG in the media, cells were removed by centrifugation, filtrated by 0.22 μm membrane, and assayed by SDS-PAGE. As shown in FIG. 1B, the band of endogenic 38-kDa protein (indicated by the arrow) from the host cell is used as an internal reference. The positions of the recombinant proteins are indicated by a bracket.

Figure 2A:
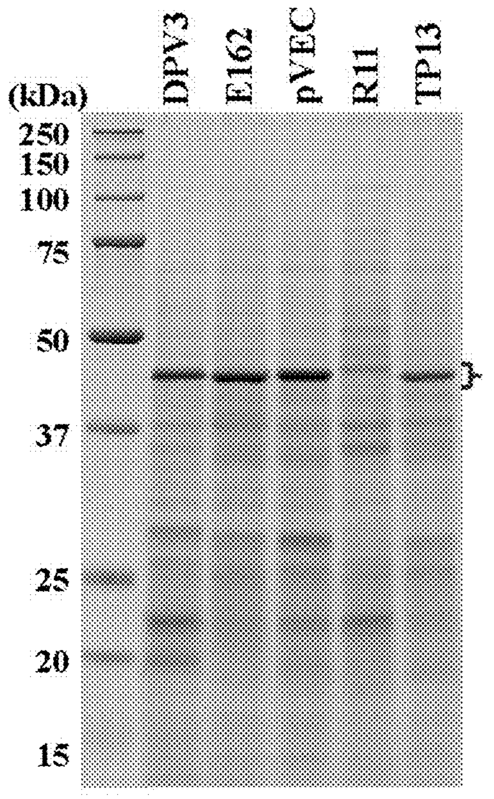
FIG. 2A shows SDS-PAGE results of *E coli.* whole cell lysates containing expressed recombinant proteins: DPV3-DsRed (DPV3), E162-DsRed (E162), pVEC-DsRed (pVEC), R11-DsRed (R11), and TP13-DsRed (TP13).
Figure 2B:
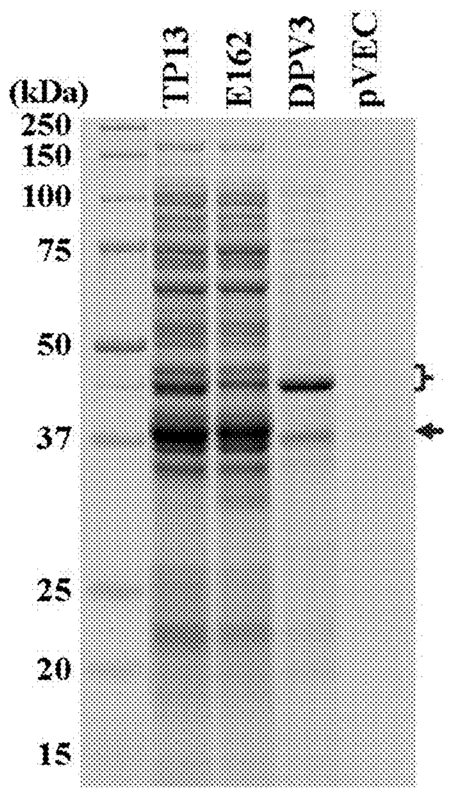
FIG. 2B shows SDS-PAGE results of culture media of the following groups: TP13-DsRed (TP13), E162-DsRed (E162), DPV3-DsRed (DPV3), and pVEC-DsRed (pVEC). Endogenic 38 kDa protein from the host cell was used as a standard molecular weight marker (indicated with an arrow). Positions of recombinant DsRed proteins are indicated with a bracket.
Figure 2C:
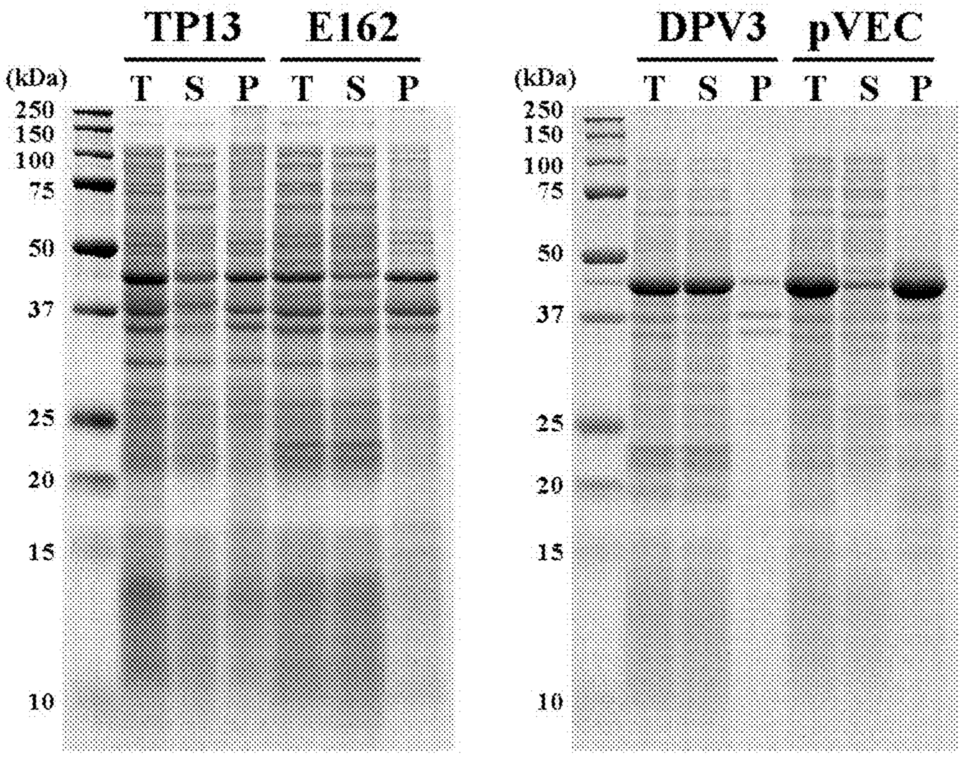
FIG. 2C shows SDS-PAGE results of *E coli.* whole cell lysates (T) containing expressed recombinant proteins: TP13-DsRed (TP13), E162-DsRed (E162), DPV3-DsRed (DPV3) and pVEC-DsRed (pVEC), centrifuged and separated into soluble (S) and insoluble (P) parts.

In the other aspect, the expression feature of CPP-J-DsRed recombinant protein is similar to CPP-DsRed recombinant proteins (see FIGS. 2A-2C). The difference resides in that the recombinant protein expression is more significant in comparison with DPV3-DsRed recombinant protein, which can be detected in the media. The secreted recombinant proteins can be isolated and purified by Ni-NTA affinity column, and in comparison with N terminal amino acid sequence identical to DPV3-J-DsRed, it was found that the secreted recombinant proteins have complete N terminal and C terminal sequences. The secreted recombinant proteins amount to about 10% of the recombinant proteins.

Figure 3:
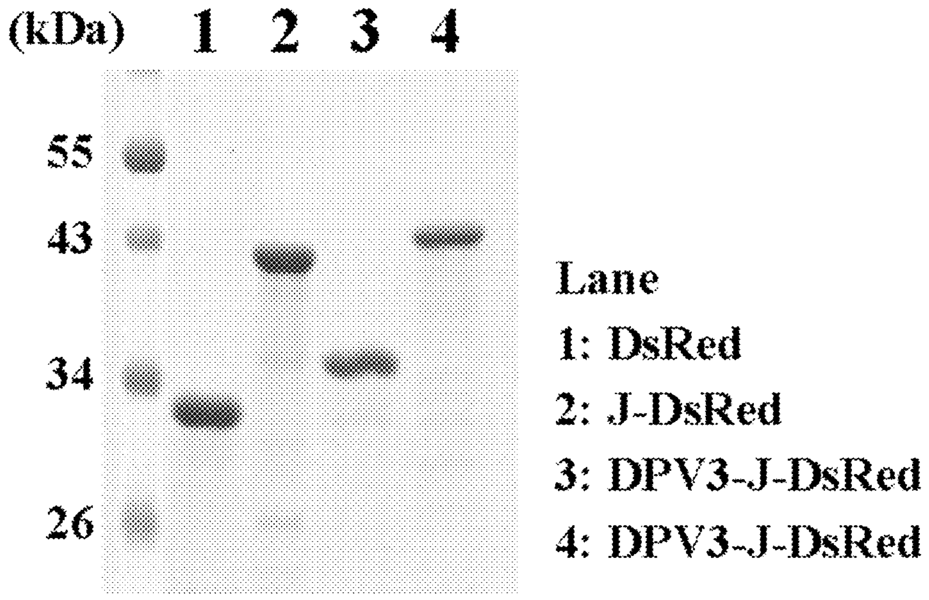
FIG. 3 shows SDS-PAGE results of *E coli.* whole cell lysates containing: DsRed, J-DsRed, DPV3-DsRed, and DPV3-J-DsRed expressed in *E Coli.* Positions of recombinant DsRed proteins are indicated with a bracket.

Further, results of DsRed, J-DsRed, DPV3-DsRed and DPV3-J-DsRed recombinant proteins analysis are shown in FIG. 3.

EXAMPLE 4

Cell Transduction Efficiency of Recombinant Proteins

Figure 4A:
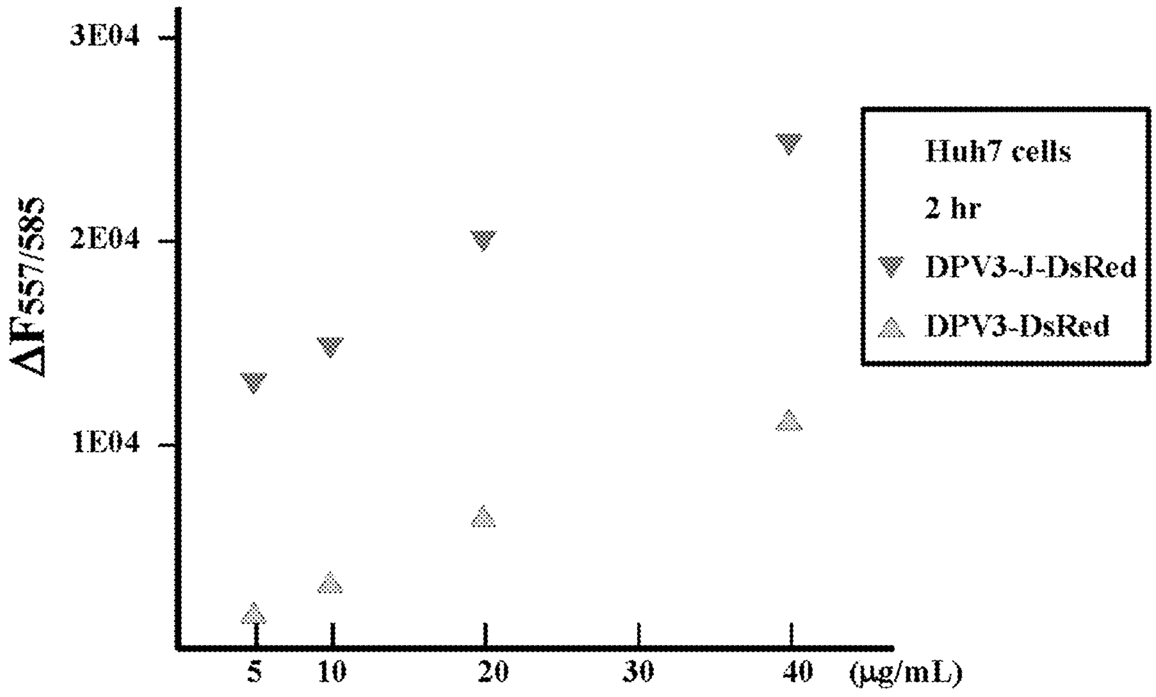
FIGS. 4A-4C show comparative results of different expression systems.
Figure 4B:
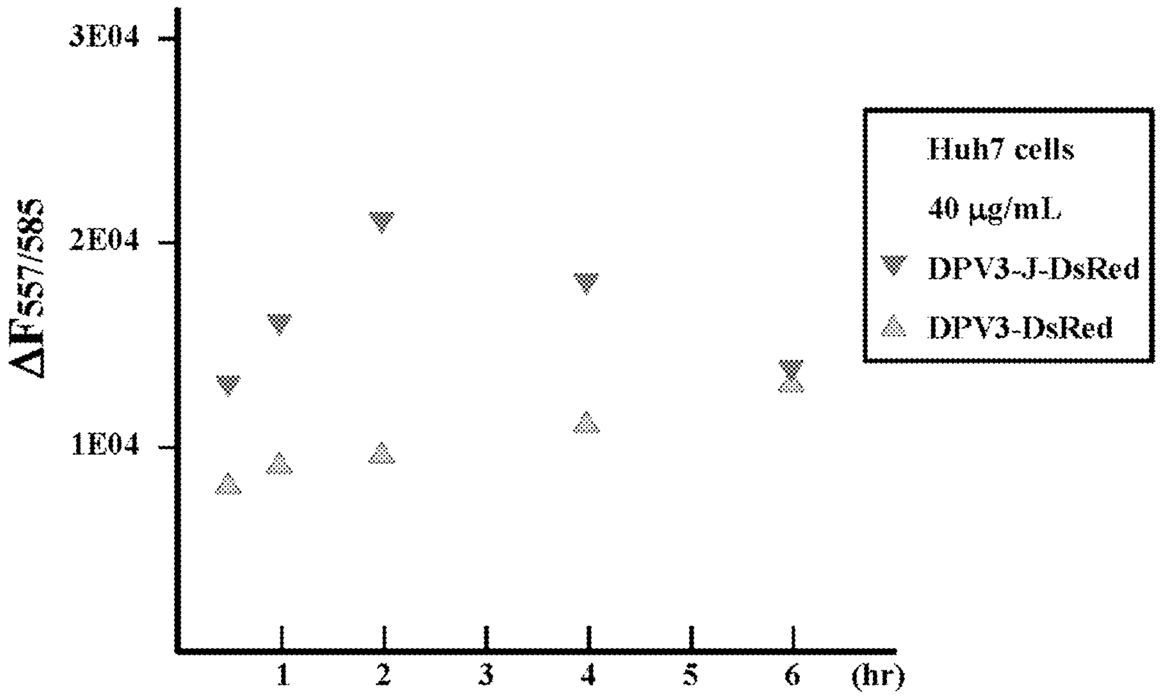
Figure 4C:
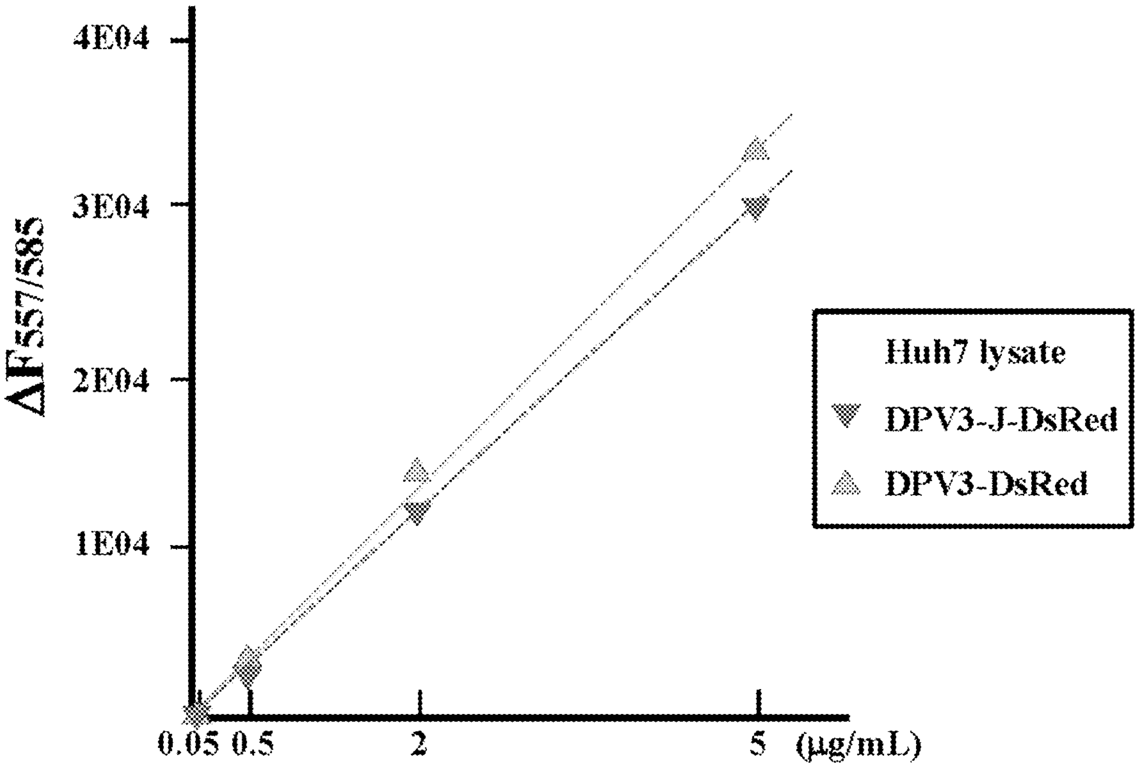

To test the transduction efficiencies of DsRed, J-DsRed, DPV3-DsRed and DPV3-J-DsRed recombinant proteins, one day prior to the experiment, $1.5\times10^5$ Huh7 cells per well were grown in a 24-well plate, and cultured by DMEM/F12 media adding 10% FCS. Culture media were removed before the experiment. The residue was washed twice with serum free medium, and then incubated with recombinant proteins of different concentrations in serum free media for specific time. The recombinant proteins not entering the cells were removed by washing twice with PBS. The cells were lyzed with PBS containing 1% Triton X-100 to release the recombinant proteins entering the cells. The sample was centrifuged at 10,000 g for 5 minutes to remove insoluble part of the cells. The supernatant was obtained and DsRed protein expression level was detected by fluorescence. The results are shown in FIGS. 4A-4C.

$1.5\times10^5$ Huh7 cells were grown in a 24-well plate. The sample was excited at 557 nm and emission intensity was detected at 585 nm to determine cell transduction efficiencies of the recombinant proteins. For FIG. 4A, different concentrations (5, 10, 20 and 40 μg/mL) of recombinant proteins DPV3-J-DsRed and DPV3-DsRed were incubated with Huh7 cells for 2 hours, and then the fluorescence intensity of DsRed in the cell was detected. For FIG. 4B, 40 μg/mL recombinant proteins DPV3-J-DsRed and DPV3-DsRed were incubated for 0.5, 1, 2, 4 or 6 hours, and then the DsRed fluorescence intensity was detected. For FIG. 4(*c*), different concentrations (0.05, 0.5, 2 and 5 μg/mL) of recombinant proteins DPV3-J-DsRed and DPV3-DsRed were incubated with Huh7 cells for 2 hours, and then the DsRed fluorescence intensity of the cell lysates were detected.

EXAMPLE 5

Effect of DPV3-J on Recombinant Protein Transduction

Figure 5:
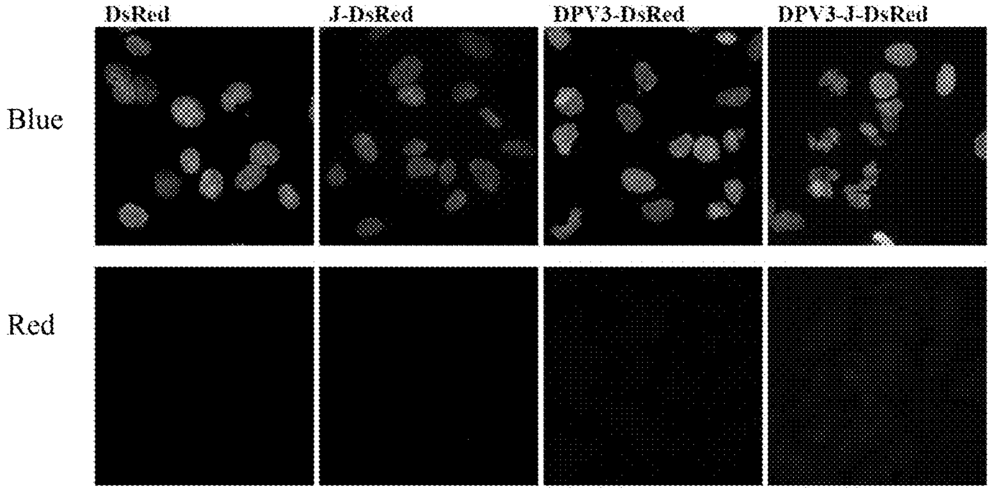
FIG. 5 shows comparative results regarding incubating DPV3-J-DsRed, DsRed, J-DsRed, or DPV3-DsRed (40 μg/mL) with Huh7 cells for 30 minutes, wherein Huh7 cells are shown in blue and the red signal represents fluorescence of DsRed. It was found that DsRed cannot enter the cells. However, red fluorescence signal can be observed in cells incubated with DPV3-J-DsRed, indicating that DPV3-J-DsRed can enter the cells.

40 μg/mL DPV3-J-DsRed, DsRed, J-DsRed and DPV3-DsRedDPV3 were incubated with Huh7 cells for 30 minutes. Cell transduction of recombinant DsRed proteins was observed by fluorescence microscopy (see FIG. 5), wherein Huh7 cells are in blue, and the red signal represents fluorescence of DsRed. It was found that DsRed itself cannot enter the cells. However, red fluorescence signal was seen in the cells incubated with DPV3-J-DsRed, indicating DPV3-J can bring DsRed into the cells.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An expression vector for expressing a recombinant protein comprising a cell penetrating peptide DPV3 and an Hsp40-J domain fused to a protein of interest in a host cell, said expression vector comprising a recombinant nucleotide sequence comprising:

a nucleotide sequence coding the DPV3;

a nucleotide sequence coding the Hsp40-J domain; and a nucleotide sequence coding the protein of interest, operatively linked to host specific transcription and translation regulatory elements for expressing the recombinant protein in the host cell, wherein the recombinant nucleotide sequence comprises SEQ ID NO: 2 in combination with SEQ ID NO: 4, or SEQ ID NO: 6 in combination with SEQ ID NO: 4.

2. The expression vector according to claim 1, wherein the recombinant protein further comprises a purification tag.

3. A host cell comprising an expression vector for expressing a recombinant protein comprising a cell penetrating peptide DPV3 and an Hsp40-J domain fused to a protein of interest in a host cell, said expression vector comprising a recombinant nucleotide sequence comprising:

a nucleotide sequence coding the DPV3;

a nucleotide sequence coding the Hsp40-J domain; and a nucleotide sequence coding the protein of interest, operatively linked to host specific transcription and translation regulatory elements for expressing the recombinant protein in the host cell, wherein the recombinant nucleotide sequence comprises SEQ ID NO: 2 in combination with SEQ ID NO: 4, or SEQ ID NO: 6 in combination with SEQ ID NO: 4.

4. The host cell according to claim 3, wherein the recombinant protein further comprises a purification tag.

5. A method for expressing a recombinant protein comprising a cell penetrating peptide DPV3, an Hsp40-J domain and a protein of interest in a host cell, comprising (a) introducing an expression vector into a host cell, said expression vector comprising a recombinant nucleotide sequence comprising: a nucleotide sequence coding the DPV3, a nucleotide sequence coding the Hsp40-J domain, and a nucleotide sequence coding the protein of interest, operatively linked to host specific transcription and translation regulatory elements for expressing the recombinant protein in the host cell, wherein the recombinant nucleotide sequence comprises SEQ ID NO: 2 in combination with SEQ ID NO: 4, or the recombinant nucleotide sequence comprises SEQ ID NO: 6 in combination with SEQ ID NO: 4;

(b) culturing the host cell in a culture medium under conditions suitable for expressing said recombinant protein; and (c) collecting said recombinant protein from the medium.

6. The method according to claim 5, wherein the recombinant protein further comprises a purification tag.

* * * * *

SEQUENCE LISTING

```
<160> NUMBER OF SEQ ID NOS: 6

<210> SEQ ID NO 1
<211> LENGTH: 16
<212> TYPE: PRT
<213> ORGANISM: Artificial Sequence
<220> FEATURE:
<223> OTHER INFORMATION: Synthesized (repeat of part of human superoxide
      dismutase)

<400> SEQUENCE: 1

Arg Lys Lys Arg Arg Arg Glu Ser Arg Lys Lys Arg Arg Arg Glu Ser
1               5                   10                  15


<210> SEQ ID NO 2
<211> LENGTH: 48
<212> TYPE: DNA
<213> ORGANISM: Artificial Sequence
<220> FEATURE:
<223> OTHER INFORMATION: Synthesized (cDNA optimized for E. coli)

<400> SEQUENCE: 2

cgcaaaaaac gccgccgcga aagccgcaaa aaacgccgcc gcgaaagc                  48


<210> SEQ ID NO 3
<211> LENGTH: 72
<212> TYPE: PRT
<213> ORGANISM: Mus musculus

<400> SEQUENCE: 3

Gly Lys Asp Tyr Tyr Gln Thr His Gly Leu Ala Arg Gly Ala Ser Asp
1               5                   10                  15
```

-continued

```
Asp Glu Ile Lys Arg Ala Tyr Arg Arg Gln Ala Leu Arg Tyr His Pro
            20                  25                  30

Asp Lys Asn Lys Glu Pro Arg Ala Glu Glu Lys Phe Lys Glu Ile Ala
        35                  40                  45

Glu Ala Tyr Asp Val Leu Ser Asp Pro Arg Lys Arg Glu Ile Phe Asp
    50                  55                  60

Arg Tyr Gly Glu Glu Gly Leu Lys
65                  70


<210> SEQ ID NO 4
<211> LENGTH: 216
<212> TYPE: DNA
<213> ORGANISM: Artificial Sequence
<220> FEATURE:
<223> OTHER INFORMATION: Synthesized (cDNA optimized for E. coli)

<400> SEQUENCE: 4

ggtaaagatt actaccagac tcacggtctc gctcgtggtg catctgatga tgaaatcaaa      60

cgtgcttacc gtcgtcaggc actgcgttac catccagaca aaaacaaaga accgcgtgca     120

gaagagaaat tcaaagagat cgcagaagca tacgacgttc tgagcgatcc acgtaaacgt     180

gaaatctccg accgttacgg tgaagaaggt ctgaaa                               216


<210> SEQ ID NO 5
<211> LENGTH: 16
<212> TYPE: PRT
<213> ORGANISM: Artificial Sequence
<220> FEATURE:
<223> OTHER INFORMATION: Synthesized (modification of SEQ ID NO: 1)

<400> SEQUENCE: 5

Ala Lys Lys Arg Arg Arg Glu Ser Arg Lys Lys Arg Arg Arg Glu Ser
1               5                   10                  15


<210> SEQ ID NO 6
<211> LENGTH: 48
<212> TYPE: DNA
<213> ORGANISM: Artificial Sequence
<220> FEATURE:
<223> OTHER INFORMATION: Synthesized (cDNA optimized for E. coli)

<400> SEQUENCE: 6

gctaaaaaac gccgccgcga aagccgcaaa aaacgccgcc gcgaaagc                    48
```